US009725422B2

(12) United States Patent
Fukuda et al.

(10) Patent No.: US 9,725,422 B2
(45) Date of Patent: Aug. 8, 2017

(54) ISOCYANURATE COMPOSITION (71) Applicant: MITSUI CHEMICALS, INC., Tokyo (JP)

(72) Inventors: Kazuyuki Fukuda, Ichihara (JP); Hideaki Otsuka, Chiba (JP); Tsutomu Yoshida, Chigasaki (JP); Tatsuya Nakashima, Takarazuka (JP); Toshiaki Moriya, Sagamihara (JP); Shirou Honma, Yokohama (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 15/123,199

(22) PCT Filed: Mar. 3, 2015

(86) PCT No.: PCT/JP2015/056254
§ 371 (c)(1),
(2) Date: Sep. 1, 2016

(87) PCT Pub. No.: WO2015/133495
PCT Pub. Date: Sep. 11, 2015

(65) Prior Publication Data
US 2017/0107186 A1    Apr. 20, 2017

(30) Foreign Application Priority Data

Mar. 4, 2014 (JP) ................................. 2014-041952
Mar. 4, 2014 (JP) ................................. 2014-041957

(51) Int. Cl.
*C07D 251/34* (2006.01)
*C07D 251/32* (2006.01)
*C08G 18/70* (2006.01)

(52) U.S. Cl.
CPC ......... *C07D 251/32* (2013.01); *C08G 18/701* (2013.01)

(58) Field of Classification Search
CPC ... C07D 251/32; C07D 251/34; C07D 251/36
See application file for complete search history.

(56) References Cited

U.S. PATENT DOCUMENTS

| 3,609,149 A * | 9/1971 | Matsui ............... C07D 251/34 528/48 |
| 4,040,992 A | 8/1977 | Bechara | |
| 4,487,928 A * | 12/1984 | Richter ............... C08G 18/791 524/100 |
| 5,102,918 A * | 4/1992 | Moriya ............... C07D 251/34 521/110 |
| 5,221,743 A * | 6/1993 | Goldstein ............ C07D 251/34 521/107 |
| 9,458,318 B2 * | 10/2016 | Greszta-Franz ... C08G 18/3876 |
| 2010/0036044 A1 | 2/2010 | Kasahara | |
| 2013/0116357 A1* | 5/2013 | Laas ................. C08G 18/3876 521/172 |
| 2013/0158145 A1 | 6/2013 | Laas | |

FOREIGN PATENT DOCUMENTS

| CN | 102134255 A * | 7/2011 |
| GB | 1234972 A | 6/1971 |
| JP | 4631531 | 9/1971 |
| JP | 52017484 A2 | 2/1977 |
| JP | 52069497 A2 | 6/1977 |
| JP | 61072013 A2 | 4/1986 |
| JP | 2013531123 | 8/2013 |
| JP | 2013532738 T2 | 8/2013 |
| WO | 2008041766 A1 | 4/2008 |
| WO | 2012010524 A1 | 1/2012 |

OTHER PUBLICATIONS

International Search Report dated Jun. 2, 2015 filed in PCT/JP2015/056254.
International Preliminary Report on Patentability dated Sep. 15, 2016 filed in PCT/JP2015/056254 total 10 pages.

* cited by examiner

*Primary Examiner* — Michael Barker
*Assistant Examiner* — Amanda L Aguirre
(74) *Attorney, Agent, or Firm* — Rankin, Hill & Clark LLP (57) ABSTRACT

The isocyanurate composition consists essentially of an isocyanurate derivative of 1,3-xylylenediisocyanate, and has a viscosity at 100° C. of 600 mPa·s or more and 20000 mPa·s or less.

4 Claims, 1 Drawing Sheet

ISOCYANURATE COMPOSITION

TECHNICAL FIELD

The present invention relates to an isocyanurate composition, i.e., a material of polyurethane resin.

BACKGROUND ART

Polyurethane resin is generally produced by reaction of polyisocyanate and an active hydrogen group-containing compound, and is widely used in various industrial fields as, for example, coatings, adhesives, and elastomers.

For polyisocyanate used in production of polyurethane resin, for example, xylylenediisocyanate (XDI) is known, and it has been proposed that xylylenediisocyanate is derived into an isocyanurate derivative to be used.

To he more specific, Patent Document 1 proposed, in Example (polyisocyanate A3), production of polyisocyanate having an isocyanurate group and an iminooxadiazinedione group, and having a viscosity at 60° C. of 8500 mPa·s by, for example, allowing m-XDI to react using a 50% concentration isopropanol/methanol (2:1) solution of tetrabutylphosphonium hydrogen difluoride as a catalyst, thereafter adding dibutylphosphate, and terminating the reaction.

CITATION LIST

Patent Document

Patent Document 1: Japanese Unexamined Patent Application Publication (Translation of PCT Application) No. 2013-532738

SUMMARY OF THE INVENTION

Problem to be Solved by the Invention

However, the polyurethane resin produced from the polyisocyanate described in the above-described Patent Document 1 has insufficient quick-drying properties.

Furthermore, further improvement in weatherability of polyurethane resin is demanded in various industrial fields.

An object of the present invention is to provide an isocyanurate composition that can produce a polyurethane resin having excellent quick-drying properties and weatherability.

Means for Solving the Problem

An isocyanurate composition of the present invention consists essentially of an isocyanurate derivative of 1,3-xylylenediisocyanate, and has a viscosity at 100° C. of 600 mPa·s or more and 20000 mPa·s or less.

In the isocyanurate composition of the present invention, it is preferable that the above-described viscosity at 100° C. is 1500 mPa·s or more and 12000 mPas or less.

In the isocyanurate composition of the present invention, it is preferable that the mononuclear isocyanurate content relative to a total amount of the above-described isocyanurate composition is 30 mass % or more and 85 mass % or less.

In the isocyanurate composition of the present invention, it is preferable that the above-described mononuclear isocyanurate content relative to a total amount of the above-described isocyanurate composition is 40 mass % or more and 70 mass % or less.

Effect of the Invention

The isocyanurate composition of the present invention can produce polyurethane resin having excellent quick-drying properties and weatherability. The produced polyurethane resin has excellent optical properties as well.

DESCRIPTION OF EMBODIMENTS

The isocyanurate composition of the present invention consists of an isocyanurate derivative of 1,3-xylylenediisocyanate (m-xylylenediisocyanate (m-XDI)). The isocyanurate composition of the present invention contains the isocyanurate derivative of 1,3-xylylenediisocyanate as the sole main component, but allows for inevitably included secondary ingredients (e.g., catalysts, promoters, and stabilizers blended in the production of isocyanurate derivative, iminooxadiazinedione derivative of 1,3-xylylenediisocyanate, 1,3-xylylenediisocyanate monomer, etc.) to be contained in the isocyanurate composition.

The isocyanurate composition of the present invention does not include isocyanurate derivative of 1,2-or 1,4-xylylenediisocyanate, and is composed only of the isocyanurate derivative of 1,3-xylylenediisocyanate.

The isocyanurate derivative of 1,3-xylylenediisocyanate is a trimer of 1,3-xylylenediisocyanate. The trimer includes symmetrical trimer, i.e., isocyanurate derivative, and an asymmetrical trimer, i.e., iminooxadiazinedione derivative, but the isocyanurate composition of the present invention consists essentially of the isocyanurate derivative of 1,3-xylylenediisocyanate, and the iminooxadiazinedione derivative of 1,3-xylylenediisocyanate may be contained, relative to a total amount of the isocyanurate composition, in an amount of, for example, 6 mass % or less, preferably 2 mass % or less, more preferably 1 mass % or less, still more preferably 0.5 mass % or less.

The isocyanurate derivative of 1,3-xylylenediisocyanate is produced by subjecting 1,3-xylylenediisocyanate to isocyanurate-forming reaction in the presence of an isocyanurate-forming catalyst.

In the present invention, the isocyanurate-forming catalyst is not particularly limited as long as it is a catalyst that activates isocyanurate formation, and examples thereof include tertiary amines such as triethylamine, tributylamine, triethylenediamine, and a secondary amine copolymer (e.g., polycondensate of secondary amines such as dialkylamine, and a monomer that is copolymerizable with secondary amines (e,g., phenol, formaldehyde, etc.)); mannich base such as 2-dimethylaminomethylphenol and 2,4,6-tris (dimethylaminomethyl) phenol; hydroxides of tetraalkylammoniums such as tetramethylammonium, tetraethylammonium, tetrabutylammonium, trimethylbenzylammonium, and tributylbenzylammonium, and organic weak acid salt thereof; hydroxides of trialkylhydroxyalkylammoniums such as trimethylhydroxypropylammonium (also called: N-(2-hydroxypropyl)-N,N,N-trimethylammonium), trimethythydroxyethylammonium, triethylhydroxypropylammonium and triethylhydroxyethylammonium, and organic weak acid salt thereof; metal salt (e.g., salt of alkali metal, magnesium salt, tin salt, zinc salt, lead salt, etc.) of alkylcarboxylic acids such as acetic acid, caproic acid, octylic acid, myristic acid, and naphthenic acid; metal chelate compounds of β-diketone such as aluminum acetylacetone and acetylacetonate; Friedel-Crafts catalysts such as aluminum chloride and boron trifluoride, various organometallic compounds such as titaniumtetrabutyrate and tributylantimonyoxide; aminosilyl-group-containing compounds such as hexamethylsilazane; and harogen substituted organic phosphorus compounds such as tetrabutylphosphonium hydrogendifluoride.

These isocyanurate-forming catalysts may be used singly or in combination of two or more.

For the isocyanurate-forming catalyst, preferably, hydroxide of tetraalkylammonium and hydroxide of trialkylhydroxyalkylammonium are used, more preferably, hydroxide of tetraalkylammonium is used, even more preferably, hydroxide of trimethylbenzylammonium, and hydroxide of tetrabutylammonium are used.

When the above-described catalyst is used as the isocyanurate-forming catalyst, 1,3-xylylenediisocyanate can be subjected to isocyanurate formation at a particularly excellent reaction rate, and therefore excellent production efficiency can be achieved.

The mixing ratio of the isocyanurate-forming catalyst relative to 100 parts by mass of the 1,3-xylylenediisocyanate is, for example, 0.001 parts by mass (phr) or more, preferably 0.015 parts by mass (phr) or more, more preferably 0.018 parts by mass (phr) or more, and for example, 0.1 parts by mass (phr) or less, preferably 0.021 parts by mass (phr) or less, more preferably 0.020 parts by mass (phr) or less.

In this method, 1,3-xylylenediisocyanate is blended with the isocyanurate-forming catalyst at the above-described mixing ratio, and the mixture is heated to cause isocyanurate-forming reaction.

The reaction conditions for the isocyanurate-forming reaction are as follows: for example, under an atmosphere of inert gas such as nitrogen gas, normal pressure (atmospheric pressure), a reaction temperature (maximum temperature reached) of, for example, 20° C. or more, preferably more than 40° C., more preferably 45° C. or more, still more preferably 60° C. or more, particularly preferably 70° C. or more, and for example, 90° C. or less, preferably 80° C. or less, more preferably 77° C. or less, still more preferably 75° C. or less. The reaction time is, for example, 30 minutes or more, preferably 60 minutes or more, more preferably 120 minutes or more, still more preferably 300 minutes or more, and for example, 720 minutes or less, preferably 600 minutes or less, more preferably 480 minutes or less.

The isocyanurate-forming catalyst can be blended at the charging stage of the isocyanurate-forming reaction (initial period), can be added during the isocyanurate-forming reaction, and the above-described mixing ratio is a total of the mixing ratio (charged ratio) of the isocyanurate-forming catalyst blended before the start of the isocyanurate-forming reaction (initial period)and the mixing ratio (added ratio) of the isocyanurate-forming catalyst added during the isocyanurate-forming reaction.

When the isocyanurate-forming catalyst is added at both of the charging stage and during reaction of the isocyanurate-forming reaction, the mixing ratio (charged ratio) of the isocyanurate-forming catalyst blended before the isocyanurate-forming reaction (initial period) relative to 100 parts by mass of 1,3-xylylenediisocyanate is, for example, 0.001 parts by mass (phr) or more, preferably 0.002 parts by mass (phr) or more, more preferably 0.003 parts by mass (phr) or more, and for example, 0.1 pans by mass (phr) or more, preferably 0.006 parts by mass (phr) or less, more preferably 0.005 parts by mass (phr) or less; and the mixing ratio (added ratio) of the isocyanurate-forming catalyst added during the isocyanurate-forming reaction relative to 100 parts by mass of 1,3-xylylenediisocyanate is, for example, 0.001 parts by mass (phr) or more, preferably 0.009 parts by mass (phr) or more, more preferably 0.012 parts by mass (phr) or more, still more preferably 0.015 parts by mass (phr) or more, and for example, 0.1 parts by mass (phr) or less, preferably 0.018 parts by mass (phr) or less, more preferably 0.017 parts by mass (phr) or less.

The ratio (charged ratio/added ratio) of the charged ratio to the added ratio of the isocyanurate-forming catalyst is, setting the total of the charged ratio and added ratio as 100, for example, 10/90 or more, preferably 15/85 or more, more preferably 17/83 or more, and for example, 40/60 or less, preferably 25/75 or less, more preferably 20/80 or less.

In the above-described reaction, to adjust the isocyanurate-forming reaction, for example, organic phosphite described in Japanese Unexamined Patent Publication No. Sho 61-129173 can be blended as a promoter.

Examples of the organic phosphite include aliphatic organic phosphite and aromatic organic phosphite.

Examples of the aliphatic organic phosphite include alkyl monophosphites such as triethyl phosphite, tributyl phosphite, tris (2-ethylhexyl) phosphite, tridecyl phosphite, trilauryl phosphite, tris (tridecyl) phosphite, and tristearyl phosphite; di, tri, or tetra phosphites derived from aliphatic polyhydric alcohols such as distearyl.pentaerythrityl.diphosphite, di.dodecyl.pentaerythritol.diphosphite, di.tridecyl.pentaerythritol.diphosphite, and tripentaerythritol.triphosphite; and furthermore, alicyclic polyphosphites such as a hydrogenated bisphenol A phosphite polymer (molecular weight 2400 to 3000), and tris (2,3-dichloropropyl) phosphite.

Examples of the aromatic organic phosphite include aryl monophosphites such as triphenyl phosphite, tris (nonylphenyl) phosphite, tris (2,4-di-t-butylphenyl) phosphite, diphenyldecyl phosphite, and diphenyl (tridecyl) phosphite; di, tri, or tetra phosphite derived from aromatic polyhydric alcohol such as dinonylphenyl.pentaerythritol.diphosphite, tetraphenyl.tetra.tridecyl.pentaerythrityl.tetra phosphite, and tetraphenyl.dipropylene glycol.diphosphite; and furthermore, diphosphites derived from bisphenol compounds such as di-alkyl having 1. to 20 carbon atoms-bisphenol A.diphosphite, 4,4'-butylidene-bis(3-methyl-6-t-butylphenyl-di.tridecyl) phosphite, These organic phosphites may be used singly or in combination of two or more.

For the organic phosphite, preferably, aromatic organic phosphite is used, more preferably, di, tri, or tetra phosphite derived from aromatic polyhydric alcohol is used, even more preferably, tetraphenyl-dipropylene glycol-diphosphite is used.

The mixing ratio of the organic phosphite relative to 100 parts by mass of the 1,3-xylylenediisocyanate is, for example, 0.01 parts by mass (phr) or more, preferably 0.03 parts by mass (phr) or more, and for example, 0.1 parts by mass (phr) or less, preferably 0.07 parts by mass (phr) or less.

By blending the above-described organic phosphite as the promoter at the above-described amount, reaction velocity and reaction rate can be improved, and gelation can be suppressed.

In the above-described reaction, stabilizers including a hindered phenol antioxidant such as 2,6-di(tert-butyl)-4-methylphenol (also called: dibutylhydroxytoluene, hereinafter may be referred to as BHT.), IRGANOX 1010, IRGANOX 1076, IRGANOX 1135, and IRGANOX 245 (all manufactured by Ciba Japan K.K., trade name) can be blended.

The mixing ratio of the stabilizer relative to 100 parts by mass of the 1,3-xylylenediisocyanate is, for example, 0.01 parts by mass (phr) or more, preferably 0.02 parts by mass (phr) or more, and for example, 0.05 parts by mass (phr) or less, preferably 0.03 parts by mass (phr) or less.

Furthermore, in the above-described reaction, as necessary, a known reaction solvent can be blended, and furthermore, a known catalyst deactivator (e.g., phosphoric acid, monochloroacetic acid, dodecylbenzenesulfonic acid, p-toluenesulfonic acid, benzoyl chloride, etc.) can be added at arbitrary timing.

Then, after completion of isocyanurate-forming reaction, the unreacted 1,3-xylylenediisocyanate monomer (when reaction solvent and/or catalyst deactivator are blended, reaction solvent and/or catalyst deactivator as well) is removed from the produced reaction mixture liquid of 1,3-xylylenediisocyanate monomer and the isocyanurate composition consisting of an isocyanurate derivative of 1,3-xylylenediisocyanate by a known method such as distillation including thin film distillation (Smith distillation), and extraction. When preparing the mixture liquid of the isocyanurate composition and 1,3-xylylenediisocyanate monomer, the reaction mixture liquid can also be used as a mixture liquid of the isocyanurate composition and 1,3-xylylenediisocyanate monomer as well without removing the unreacted 1,3-xylylenediisocyanate monomer.

In the present invention, when thin film distillation is performed after completion of isocyanurate-forming reaction of 1,3-xylylenediisocyanate, the isocyanurate composition yield (distillation yield) produced by the thin film distillation is a mass of the isocyanurate composition relative to the mass of the reaction mixture liquid, and is, for example, 16 mass % or more, preferably 25 mass % or more, more preferably 40 mass % or more, and for example, 64 mass % or less, preferably 60 mass % or less.

The distillation yield of the isocyanurate composition can be obtained in conformity with Examples described later, by calculating the ratio of the mass of the isocyanurate composition relative to the mass of the reaction mixture liquid.

Furthermore, in the present invention, in the isocyanurate-forming reaction, the active hydrogen group-containing compound (described later) is not blended as the modifier and the isocyanurate derivative is not modified by the active hydrogen group-containing compound (described later) as the modifier. That is, the isocyanurate derivative is produced from only 1,3-xylylenediisocyanate.

The isocyanurate composition, particularly the isocyanurate composition consisting of an isocyanurate derivative that is composed only of 1,3-xylylenediisocyanate and that is not modified with the active hydrogen group-containing compound (described later) as the modifier (hereinafter may be referred to as "unmodified") be produced in this manner.

With the unmodified isocyanurate composition consisting of an isocyanurate derivative of 1,3-xylylenediisocyanate, polyurethane resin (described later) with excellent weatherability (e.g., gloss retention, etc.) can be produced.

In the present invention, the unmodified isocyanurate derivative is defined as a derivative in which an active hydrogen group-containing compound (described later) is not blended intendedly as a modifier, and allows a modification group (e.g., urethane group, urea group, etc.) for the isocyanurate derivative of 1,3-xylylenediisocyanate, based on, for example, an active hydrogen group-containing compound unavoidably mixed in (described later)(e.g., solvent of isocyanurate-forming catalyst (e.g., methanol, etc.), moisture, etc.) at the time of isocyanurate derivative production to be contained.

The modification group concentration allowed in the isocyanurate derivative of 1,3-xylylenediisocyanate relative to 1g of the mass of the isocyanurate derivative of 1,3-xylylenediisocyanate is, for example, 0.02 mmol or less, preferably 0.011 mmol or less, more preferably 0.005 mmol or less.

The modification group concentration of the isocyanurate derivative of 1,3-xylylenediisocyanate can be calculated by, for example, $^1$H-NMR measurement, In the following, unless otherwise noted, the isocyanurate derivative is an unmodified isocyanurate derivative.

The isocyanurate composition has an isocyanate group concentration (solid content 100 wt %) of, for example, 15.0 mass % or more, preferably 160 mass % or more, more preferably 20.0 mass % or more, and for example, 22.0 mass % or less, preferably 21.0 mass % or less.

The isocyanate group concentration (solid content 100 wt %) of the isocyanurate composition can be determined in conformity with Examples described later.

The isocyanurate composition has an isocyanate monomer concentration (unreacted 1,3-xylylenediisocyanate concentration) of, for example, 2 mass % or less, preferably 1 mass % or less, more preferably 0.5 mass % or less.

In the reaction for producing the isocyanurate composition (isocyanurate-forming reaction), the isocyanate group conversion rate (reaction rate) is, for example, 8 mass % or more, preferably 10 mass % or more, more preferably 15 mass % or more, and for example, 43 mass % or less, preferably 40 mass % or less, more preferably 35 mass % or less.

Furthermore, in view of improving optical properties and weatherability, the isocyanate group conversion rate (reaction rate) in the reaction for producing the isocyarnrate composition is preferably 8 mass % or more, more preferably 10 mass % or more, preferably 38 mass % or less, more preferably less than 35 mass %, still more preferably less than 30 mass %, particularly preferably 20 mass % or less.

In view of improving quick-drying properties, the isocyanate group conversion rate (reaction rate) in the reaction for producing the isocyanurate composition is preferably 30 mass % or more, more preferably 35 mass % or more, and preferably 43 mass % or less, more preferably 40 mass % or less.

In the present invention, the isocyanate group conversion rate (reaction rate) in the reaction for producing the isocyanurate composition is substantially the same as the isocyanurate conversion rate in the reaction for producing the isocyanurate composition.

In the reaction for producing the isocyarmrate composition, the isocyanate group conversion rate (reaction rate) can be determined by calculating the reduction rate of the isocyanate group concentration relative to the isocyanate group concentration in the charged liquid (including 1,3-xylylenediisocyanate, promoter, stabilizer, and as necessary, reaction solvent) in conformity with Examples described later.

The isocyanurate composition includes a mononuclear isocyanurate (to be specific, a compound in which 3 molecules of 1,3-xylylenediisocyanate form one isocyanurate ring, and the isocyanurate ring is not bonded with other isocyanurate ring, that is, 3 molecules of 1,3-xylylenediisocyanate via one isocyanurate ring) and a polynuclear isocyanurate (e.g., dinuclear isocyanurate (to be specific, a compound in which one mononuclear isocyanurate is bonded with another mononuclear isocyanurate), tri (or more) nuclear isocyanurate (to be specific, a compound in which three or more mononuclear isocyanurates are bonded), etc.).

The mononuclear isocyanurate content relative to a total amount of the isocyanurate composition of 1,3-xylylenediisocyanate is, for example, 30 mass % or more, preferably 40 mass % or more, more preferably 45 mass % or more, still more preferably 55 mass % or more, particularly preferably 65 mass % or more, and for example, 85 mass % or less, preferably 80 mass % or less, more preferably 70 mass % or less.

When the mononuclear isocyanurate content is within the above-described range, a polyurethane resin having excellent optical properties, quick-drying properties, and weatherability (described later) can be produced. Furthermore, when the mononuclear isocyanurate content is the above-described lower limn or more, a polyurethane resin with excellent optical properties (described later) can be produced, and when the mononuclear isocyanurate content is the above-described upper limit or less, polyurethane resin with excellent quick-drying properties (described later) can be produced.

Furthermore, in view of improving optical properties, the mononuclear isocyanurate content relative to a total amount of the isocyanurate composition is preferably 42 mass % or more, more preferably 51 mass % or more, still more preferably 65 mass % or more, and preferably 85 mass % or less.

Furthermore, in view of improvement in quick-drying properties, the mononuclear isocyanurate content relative to a total amount of the isocyanurate composition's preferably 30 mass % or more, preferably 52 mass % or less, more preferably 45 mass % or less.

The mononuclear isocyanurate content can be determined by gel permeation chromatography (GPC) in conformity with Examples described later.

That is, in the chromatogram when the isocyanurate composition is subjected to gel permeation chromatograph measurement, the area percentage of a peak area having peak top between the polystyrene-based molecular weight of 400 to 1000, preferably 600 to 900 relative to the total peak area thereinafter trimolecular product area percentage) corresponds to the mononuclear isocyanurate content relative to a total amount of the isocyanurate composition.

The trimolecular product area percentage can be calculated as a peak area ratio in the obtained chromatogram (chart) by measuring the molecular weight distribution of the isocyanurate composition with a gel permeation chromatograph (GPC) equipped with a refractive index detector (RID) in conformity with Examples described later.

The isocyanurate composition has a viscosity at 100° C. of (solid content 100 wt %) 600 mPa·s or more, preferably 800 mPa·s or more, more preferably 1500 mPa·s or more, still more preferably 2000 mPa·s or more and 20000 mPa·s or less, preferably 15000 mPa·s or less, more preferably 12000 mPa·s or less, still more preferably 9000 mPa·s or less, still more preferably 7000 mPa·s or less, still more preferably 5000 mPa·s or less, particularly preferably 3000 mPa·s or less.

When the isocyanurate composition has a viscosity at 100° C. (solid content 100 wt %) within the above-described range, polyurethane resin with excellent weatherability (described later) can be produced. When the isocyanurate composition has a viscosity at 100° C. of (solid content 100 wt %) the above-described lower limit or more, the polyurethane resin with excellent optical properties (described later) can be produced, and when the isocyanurate composition has a viscosity at 100° C. of the above-described upper limit or less, polyurethane resin with excellent quick-drying properties described later) can be produced.

In view of improving optical properties, the isocyanurate composition has a viscosity at 100° C. of (solid content 100 wt %) preferably 600 mPa·s or more, more preferably 800 mPa·s or more, preferably less than 8000 mPa·s, more preferably 2500 mPa·s or less, still more preferably 1500 mPa·s or less.

In view of improving quick-drying properties, the isocyanurate composition has a viscosity at 100° C. of (solid content 100 wt %) preferably 5000 mPa·s or more, more preferably 7000 mPa·s or more, more preferably 8000 mPa·s or more, and preferably 20000 mPa·s or less, more preferably 19500 mPa·s or less.

The isocyanurate composition has a viscosity at 80° C. of (solid content 100 wt %), for example, 2500 mPa·s or more, preferably 5000 mPa·s or more, and for example, 150000 mPa·s or less, preferably 100000 mPa·s or less.

The isocyanurate composition has a viscosity at 60° C. of (solid content 100 wt %), for example, 9000 mPa·s or more, preferably 30000 mPa·s or more, and for example, 100000 mPa·s or less.

The viscosity at a specific temperature (at 100° C., 80° C., and 60° C.) of the isocyanurate composition can be measured in conformity with Examples described later.

To the isocyanurate composition, as necessary, a compound containing a sulfonamide group can be added.

For the compound containing a sulfonamide group, for example, aromatic sulfonamides and aliphatic sulfonamides are used.

Examples of aromatic sulfonamides include benzene sulfonamide, dimethyl benzene sulfonamide, sulfanilamide, o- and p-toluene sulfonamide, hydroxynaphthalene sulfonamide, naphthalene-1-sulfonamide, naphthalene-2-sulfonamide, m-nitrobenzene sulfonamide, and p-chlorobenzene sulfonamide.

Examples of aliphatic sulfonamides include methane sulfonamide, N,N-dimethylmethane sulfonamide, N,N-dimethyl ethane sulfonamide, N,N-diethylmethane sulfonamide, N-methoxymethane sulfonamide, N-dodecylmethane sulfonamide, N-cyclohexyl-1-butanesulfonamide, and 2-aminoethane sulfonamide.

These compounds containing sulfonamide groups may be used singly or in combination of two or more.

As the compound containing a sulfonamide group, preferably, aromatic sulfonamides are used, more preferably, o- or p-toluene sulfonamides are used.

Relative to 100 parts by mass of the isocyanurate composition, 0,001 to 0.5 parts by mass, preferably 0.005 to 0.4 parts by mass, more preferably 0.01 to 0.3 parts by mass of the compound containing a sulfonamide group is added.

When the compound containing a sulfonamide group is added at the above-described amount, improvement in storage stability of the polyisocyanurate composition can be achieved.

The isocyanurate composition does not contain a solvent, but as necessary, by diluting the isocyanurate composition with an organic solvent, the isocyanurate composition can be prepared as a diluted solution of the isocyanurate composition.

Examples of the organic solvent include ketones such as acetone, methyl ethyl ketone, methylisobutylketone, and cyclohexanone; nitriles such as acetinitrile; alkylesters such as methyl acetate, ethyl acetate, butyl acetate, and isobutyl acetate; aliphatic hydrocarbons such as n-hexane, n-heptane, and octane; alicyclic hydrocarbons such as cyclohexane and methylcyclohexane; aromatic hydrocarbons such as toluene, xylene, and ethylbenzene; glycol etheresters such as methylcellosolveacetate, ethylcellosolveacetate, methylcarbitolacetate, ethylcarbitolacetate, ethylene glycolmonoethyletheracetate, propylene glycolmonomethyletheracetate, 3-methyl-3-methoxybutylacetate, and ethyl-3-ethoxypropionate; ether such as diethylether, tetrahydrofuran, and dioxane; halogenated aliphatic hydrocarbons such as methyl chloride, methylene chloride, chloroform, carbon tetrachloride, methyl bromide, methylene iodide, and dichloroethane; polar aprotics such as N-methylpyrrolidone, dimethylformamide, N,N-dimethylacetamide, dimethyl sulfoxide, and hexamethyl phosphor amide.

Examples of organic solvents also include nonpolar solvents (nonpolar organic solvents), and examples of nonpolar solvents include those nonpolar organic solvents having an aniline point of, for example, 10 to 70° C., preferably 12 to 65° C. and having low toxicity and solvency, such as aliphatic, naphthene hydrocarbon organic solvent; and vegetable oils typically represented by turpentine oil.

The nonpolar organic solvents can be obtained from commercially available products, and examples of those commercially available products include petroleum hydrocarbon organic solvents such as Haws (manufactured by Shell Chemicals, aniline point 15° C.). Swasol 310 (manufactured by Maruzen Petrochemical, aniline point 16° C.), Esso Naphtha No. 6 (manufactured by Exxon Mobil Chemical, aniline point 43° C.), Laws (manufactured by Shell Chemicals, aniline point 43° C.), Esso Naphtha No. 5 (manufactured by Exxon Mobil Corporation, aniline point 55° C.), and pegasol 3040 (manufactured by Exxon Mobil Corporation, aniline point 55° C.); and also methylcyclohexane (aniline point 40° C.), ethylcyclohexane (aniline point 44° C.), and turpentine oils such as gum turpentine N (manufactured by YASUHARA CHEMICAL CO., LTD., aniline point 27° C.), These organic solvents may be used singly or in combination of two or more.

The isocyanurate composition is diluted by mixing the isocyanurate composition with these organic solvents at an arbitrary ratio. The diluted solution of the isocyanurate composition can be prepared in this manner.

When the diluted solution of the isocyanurate composition is prepared, for example, an organic solvent can be blended with the isocyanurate derivative of 1,3-xylylenediisocyanate in advance, or the organic solvent can be blended separately with the isocyanurate composition.

When the diluted solution of the isocyanurate composition is prepared, the polyisocyanurate composition concentration relative to the total amount of the diluted solution is, for example, 20 mass % or more, preferably 30 mass % or more, and for example, 95 mass % or less, preferably 90 mass % or less.

The diluted solution of the isocyanurate composition has a viscosity at 25° C. (measured with B-type viscometer) of, for example, 10 mPa·s or more, preferably 20 mPa·s or more, and for example, 10000 mPa·s or less, preferably 5000 mPa·s or less.

Such an isocyanurate composition consists essentially of an isocyanurate derivative of 1,3-xylylenediisocyanate, and has a viscosity at 100° C. of 600 mPa·s or more and 2000 mPa·s or less.

Therefore, with such an isocyanurate composition, polyurethane resin having excellent optical properties, quick-drying properties, and weatherability can be produced.

Therefore, the isocyanurate composition is suitably used in polyurethane resin production.

The isocyanurate composition can be mixed with a monomer and/or derivative of other polyisocyanate, when a polyurethane resin to be described next is produced.

Examples of the other polyisocyanate include known or widely used polyisocyanates such as aliphatic polyisocyanate (including alicyclic polyisocyanate), aromatic polyisocyanate, and araliphatic polyisocyanate.

The polyurethane resin can be produced by allowing the polyisocyanate component including the above-described isocyanurate composition to react with the active hydrogen group-containing compound-containing component.

The polyisocyanate component include the above-described isocyanurate composition, and as necessary, a monomer and/or derivative of the above-described other polyisocyanate, Examples of the active hydrogen group-containing compound-containing component include a polyol component, a polythiol component, and a polyamine component, and preferably, a polyol component is used.

Examples of polyol component in the present invention include low-molecular-weight polyols and high-molecular weight polyols.

The low molecular-weight polyol is a compound having two or more hydroxyl groups and a number average molecular weight of generally 40 or more and less than 300, preferably less than 400, and examples thereof include dihydric alcohols such as ethylene glycol, propylene glycol, 1,3-propanediol, 1,4-butyleneglycol, 1,3-butyleneglycol, 1,2-butyleneglycol, 1,5-pentanediol, 1,6-hexanediol, neopentyl glycol, 3-methyl-1,5-pentanediol, 2,2,2-trimethylpentanediol, 3,3-dimethylolheptane, alkane (C 7 to 20) diol, 1,3-or 1,4-cyclohexanedimethanol and a mixture thereof, 1,3-or 1,4-cyclohexanediol and a mixture thereof, hydrogenated bisphenol A, 1,4-dihydroxy-2-butene, 2,6-dimethyl-1-octene-3,8-diol, bisphenol A, diethylene triethylene glycol, and dipropylene glycol; trihydric alcohols such as glycerin, trimethylolpropane, and triisopropanolamine; tetrahydric alcohols such as tetramethylolmethane (pentaerythritol) and diglycerol; pentahydric alcohols such as xylitol; hexahydric alcohols such as sorbitol, mannitol, allitol, iditol, dulcitol, altritol, inositol, and dipentaerythritol; heptahydric alcohols such as perseitol; and octahydric alcohols such as sucrose.

These low molecular-weight polyols may be used singly or in combination of two or more.

The high molecular weight polyol is a compound having two or more hydroxyl groups and a number average molecular weight of 300 or more, preferably 400 or more, still more preferably 500 or more, and generally 20000 or less, preferably 10000 or less, and examples thereof include polyetherpolyol (e.g., polyoxyalkylenepolyol, polytetramethylene ether polyol, etc.), polyesterpolyol (e.g., adipic acid polyesterpolyol, phthalic acid polyesterpolyol, lactone polyesterpolyol, etc.), polycarbonatepolyol, polyurethane polyol (e.g., polyol produced by subjecting, for example, polyetherpolyol, polyesterpolyol, or polycarbonatepolyol to urethane modification with polyisocyanate), epoxy polyol, vegetable oil polyol, polyolefinpolyol, acrylic polyol, and vinyl monomer-modified polyol.

These high molecular weight polyols may be used singly or in combination of two or more.

For the high molecular weight polyol, acrylic polyol is preferably used.

Then, to produce the polyurethane resin by allowing the above-described isocyanurate composition to react with the above-described active hydrogen group-contain/g compound, for example, the isocyanurate composition and the active hydrogen group-containing compound are blended and polymerized so that the equivalent ratio (NCO/active hydrogen group) of the isocyanate group in the isocyanurate composition relative to the active hydrogen group in the active hydrogen group-containing compound (e.g., hydroxyl group, mercapto group, am group, etc.) is, for example, 0.75 to 1.3, preferably 0.9 to 1.1.

For the polymerizatio method, for example, bulk polymerization, and solution polymerization are used.

In bulk polymerization, for example, the active hydrogen group-containing compound is added to the isocyanurate composition while stirring the isocyanurate composition under nitrogen flow, and reaction is allowed to occur at a reaction temperature of 50 to 250° C., even more preferably 50 to 200° C., for about 0.5 to 15 hours.

In the solution polymerization, the isocyanurate composition and the active hydrogen group-containing compound are added to an organic solvent of those organic solvents used for the above-described dilution of the isocyanurate composition, and the mixture is allowed to react at a reaction temperature of 50 to 120° C., preferably 50 to 100° C., for about 0.5 to 15 hours.

Furthermore, in the above-described polymerization reaction, as necessary, for example, a known urethane-forming catalyst such as amines and an organometallic compound may be added.

Examples of amines include tertiary amines such as triethylamine, triethylenediamine, bis-(2-dimethylaminoethyl) ether, and N-methylmorpholine; quaternary ammonium salts such as tetraethyl hydroxyl ammonium; and imidazoles such as imidazole and 2-ethyl-4-methylimidazole.

Examples of organometallic compounds include organic tin compounds such as tin acetate, stannous octoate, stannous oleate, tin laurate, dibutyl tin diacetate, dimethyl tin dilaurate, dibutyl tin dilaurate, dibutyl tin dimercaptide, dibutyl tin maleate, dibutyl tin dilaurate, dibutyl tin dineodecanoate, dioctyl tin dimercaptide, dioctyl tin dilaurylate, and dibutyl tin dichloride; organic lead compounds such as lead octanoate and lead naphthenate; organic nickel compound such as nickel naphthenate; organic cobalt compounds such as cobalt naphthenate; organic copper compounds such as copper octenate; organic bismuth compounds such as bismuth octylate and bismuth neodecanoate.

Examples of urethane-forming catalysts also include potassium salts such as potassium carbonate, potassium acetate, and potassium octoate.

These urethane-forming catalysts may be used singly or in combination of two or more.

Further, when the above polymerization reaction is more industrially carried out, the polyurethane resin can be obtained by a known process such as one shot process and prepolymer process.

In the one shot process, for example, the isocyanurate composition and the active hydrogen group-containing compound are formulated (mixed) so that the equivalent ratio (NCO/active hydrogen group) of the isocyanate group in the isocyanurate composition relative to the active hydrogen group in the active hydrogen group-containing compound (e.,c;., hydroxyl group, mercapto group, amino group, etc.) is, for example, 0.75 to 1.3, preferably 0.9 to 1.1, and thereafter curing reaction is allowed to occur at, for example, room temperature (e.g., 25° C., the same applies to the following) to 250° C., preferably, room temperature to 200° C., for, for example, 5 minutes to 72 hours, preferably 4 to 24 hours. The curing temperature may be a constant temperature, or may be increased/decreased stepwise.

In the prepolymer process, for example, first, the isocyanurate composition is allowed to react with a portion of the active hydrogen group-containing compound (preferably, high molecular weight polyol) to synthesize an isocyanate group-terminated prepolymer having an isocyanate group at the terminal of the molecule. Then, the produced isocyanate group-terminated prepolymer is allowed to react with the remaining portion of the active hydrogen group-containing compound (preferably, low molecular-weight polyol and/or polyamine component) to cause chain extension reaction. In the prepolymer process, the remaining portion of the active hydrogen group-containing compound is used as the chain extender.

To synthesize the isocyanate group-terminated prepolymer, the isocyanurate composition is formulated (mixed) with a portion of the active hydrogen group-containing compound so that the equivalent ratio (NCO/active hydrogen group) of the isocyanate group in the isocyanurate composition relative to the active hydrogen group in the portion of the active hydrogen group-containing compound is, for example, 1.1 to 20, preferably 1.3 to 10, still more preferably 1.3 to 6, and the mixture is allowed to react in a reaction vessel at, for example, room temperature to 150° C., preferably 50 to 120° C., for, for example, 0.5 to 18 hours, preferably 2 to 10 hours. In this reaction, as necessary, the above-described urethane-forming catalyst may be added, and after the completion of the reaction, as necessary, the unreacted polyisocyanurate composition can be removed, for example, by a known removal method such as distillation and extraction.

Then, to allow the produced isocyanate group-terminated prepolymer to react with the remaining portion of the active hydrogen group-containing compound, the isocyanate group-terminated prepolymer is formulated (mixed) with the remaining portion of the active hydrogen group-containing compound so that the equivalent ratio (NCO/active hydrogen group) of the isocyanate group in the isocyanate group-terminated prepolymer relative to the active hydrogen group in the remaining portion of the active hydrogen group-containing compound is, for example, 0.75 to 1.3, preferably 0.9 to 1.1, and curing reaction is allowed to occur at, for example, room temperature to 250° C., preferably, room temperature to 200° C. for, for example, 5 minutes to 72 hours, preferably 1 to 24 hours.

The polyurethane resin can be produced in this manner.

When the polyurethane resin is produced, as necessary, known additives, for example, a plasticizer, an anti-blocking agent, a heat-resistant stabilizer, a light stabilizer, an antioxidant, a mold release agent, a catalyst, and furthermore, a pigment, a dye, a lubricant, a filler, and a hydrolysis prevention agent can be further added at a suitable ratio. These additives may be added at the time of synthesizing components, or may be added at the time of mixing and dissolving components, or may be added after the synthesis.

The polyurethane resin is produced by using the isocyanurate composition of the present invention, and therefore has excellent optical properties, weatherability, and quick-drying properties, That is, the polyurethane resin produced by using the isocyanurate composition of the present invention has a haze (measured in conformity with Examples described later) of, for example, 0.3 or more and 5.4 or less, preferably 5.0 or less, more preferably 2.1 or less, still more preferably 1.3 or less, particularly preferably 1.1 or less, particularly preferably 0.4 or less.

The polyurethane resin produced by using the isocyanurate composition of the present invention has a set-to-touch drying time (measured in conformity with Examples described later) of, for example, 90 seconds or more, and for example, 145 seconds or less, preferably 135 seconds or less, more preferably 115 seconds or less, still more preferably 100 seconds or less, particularly preferably 95 seconds or less.

The polyurethane resin produced by using the isocyanurate composition of the present invention has a through-dry time (measured in conformity with Examples described later) of, for example, 85 minutes or more, and for example, 120 minutes or less, preferably 105 minutes or less, more preferably 95 minutes or less, still more preferably 90 minutes or less.

The polyurethane resin produced by using the isocyanurate composition of the present invention has a gloss retention (measured in conformity with Examples described later) of, for example, 81% or more, preferably 83% or more, more preferably 88% or more, still more preferably 90% or more, and for example, 91% or less.

Therefore, such a polyurethane resin can be widely used in various fields such as, for example, a film coating agent, various inks, adhesives, sealing agents, various microcapsules, plastic lens, artificial and synthetic leather, RIM product, slush powder, elastic molded articles (spandex), and urethane foam.

Polyurethane resin (coating resin) produced by using the isocyanurate composition of the present invention can also be produced from a two-component curable polyurethane composition.

The two-component curable polyurethane composition includes a polyisocyanate component prepared as the curing agent, and a polyol component prepared as the main component.

The polyisocyanate component (curing agent) contains the above-described isocyanurate composition of the present invention.

The polyisocyanate component (curing agent) can contain, as necessary, a monomer and/or derivative of the above-described other polyisocyanate and the above-described organic solvent.

When the polyisocyanate component (curing agent) contains an organic solvent, the organic solvent content is not particularly limited, and is set suitably in accordance with the purpose and application.

For the polyol component main component), the above-described polyol component s used. The polyol component may be used singly or in combination of two or more. For the polyol component, preferably, a high molecular weight polyol is used, even more preferably, acrylic polyol is used.

The polyol component (main component) can contain, as necessary, the above-described organic solvent.

When the polyol component (main component) contains the organic solvent, the organic solvent content is not particularly limited, and is set suitably in accordance with the purpose and application.

In the two-component curable polyurethane composition, the polyisocyanate component (curing agent) is separately prepared from the polyol component (main component), and they are blended and mixed at the time of their use.

The mixing ratio of the polyisocyanate component (curing agent) to the polyol component (main component is adjusted so that the equivalent ratio (OH/NCO) of the hydroxyl group in the polyol component (main component) relative to the isocyanate group in the polyisocyanate component (curing agent) is, for example, 0.5 or more, preferably 0.75 or more, and for example, 2 or less, preferably 1.5 or less.

To one or both of the polyisocyanate component (curing agent) and the polyol component (main component), as necessary, for example, additives such as epoxy resin, a catalyst, a coating improving agent, a leveling agent, an antifoaming agent, stabilizers including an antioxidant, and an ultraviolet absorber, a plasticizer, a surfactant, a pigment (e.g., titanium oxide), a filler, organic or inorganic microparticles, an antimold agent, and a silane coupling agent can be blended. These additives are blended in an amount suitable for its purpose and use.

The two-component curable polyurethane composition is produced by using the isocyanurate composition of the present invention, and therefore has excellent optical properties, quick-drying properties, and weatherability.

Therefore, the two-component curable polyurethane composition is suitably used in various fields such as paint (plastic paint, automotive paint), adhesives, coating agents, inks, and sealants.

EXAMPLES

In the description below, specific numeral values such as mixing ratios (content), physical property values, and parameters can be replaced with the corresponding upper limit values (numeral values defined with "or less" and "less than") or lower limit values (numeral values defined with "or more" and "more than") of the mixing ratio (content), physical property values, and parameters in the above-described "DESCRIPTION OF EMBODIMENTS".

The measurement methods used in Examples and Comparative Examples are described below.

<Isocyanurate Composition Distillation Yield>

The isocyanurate composition distillation yield was determined by measuring the mass of the reaction mixture liquid (liquid before distillation) and the mass of the isocyanurate composition (liquid after distillation), and by calculating the ratio of the mass of the isocyanurate composition relative to the mass of the reaction mixture liquid.

Isocyanurate composition distillation yield (mass %)=(mass of the isocyanurate composition (g)/ mass of the reaction mixture liquid (g))×100

<Isocyanate Group Concentration (Mass %) and Isocyanate Group Conversion Rate Reaction Rate)(Mass %)>

The isocyanate group concentration of the charged liquid, reaction mixture liquid, and isocyanurate composition was measured in conformity with n-dibutylamine method of JIS K-1556 (2006).

The isocyanate group conversion rate (reaction rate) in the isocyanurate-forming reaction was determined by calculating the isocyanate group concentration reduction rate relative to the isocyanate group concentration of the charged liquid.

Isocyanate group concentration reduction rate (mass %)=((isocyanate group concentration of charged liquid (mass %)-isocyanate group concentration of the reaction mixture liquid (mass %))/isocyanate group concentration of charged liquid (mass %))×100

The isocyanate group conversion rate is the isocyanurate conversion rate.

<Mononuclear Isocyanurate Content (Mononuclear Content)(Mass %)>

A sample of the isocyanurate composition was subjected to gel permeation chromatography (GPC) measurement, and the trimolecular product area percentage was obtained from the obtained chromatogram (chart) based on the area percentage of the peak area having peak top between polystyrene-based molecular weight of 400 to 1000 relative to the total peak area, and the trimolecular product area percentage was defined as the mononuclear isocyanurate content (mononuclear content) relative to the total amount of the isocyanurate composition.

Figure 1:
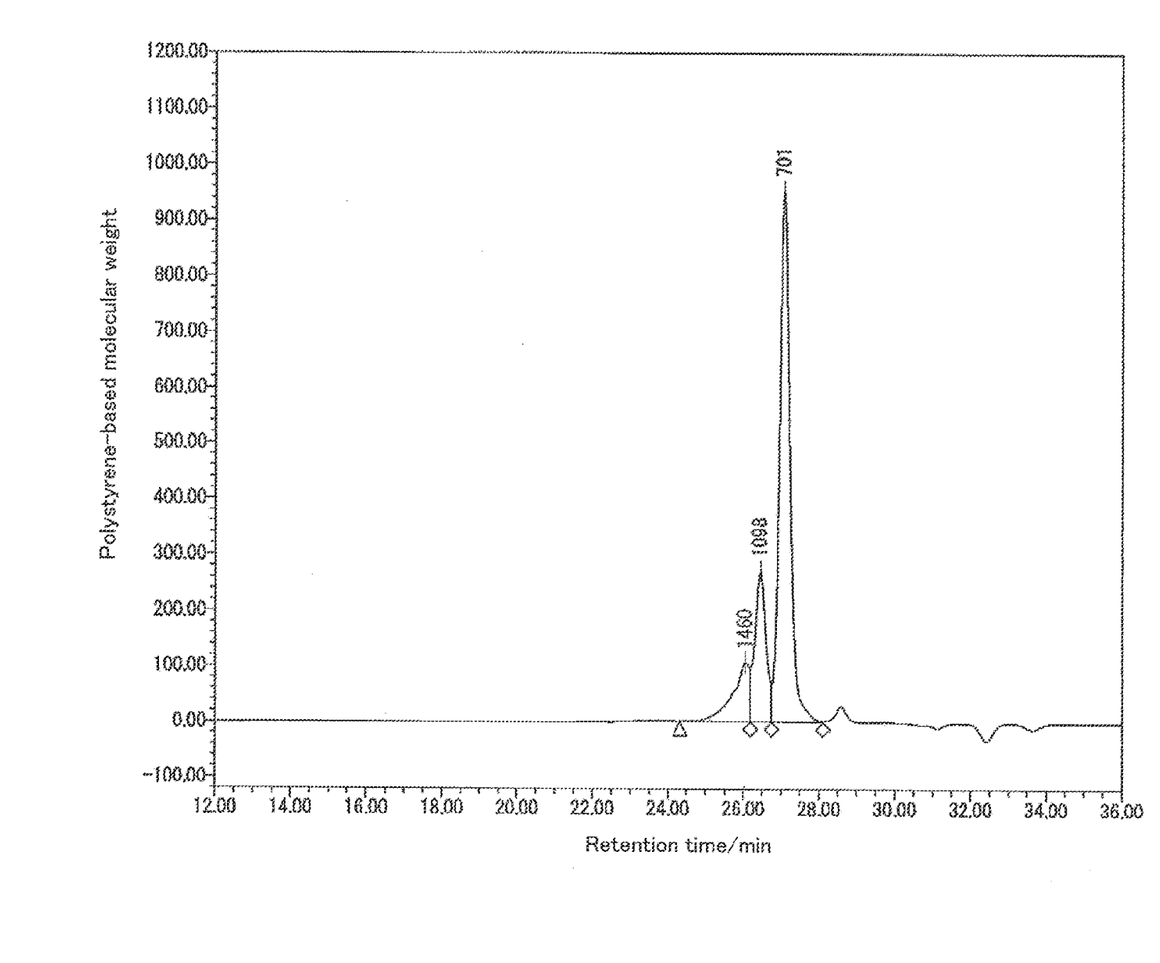
FIG. 1 is a gel permeation chromatogram of the isocyanurate composition of Example 3.

The trimolecular product area percentage is, in the chromatogram (chart) obtained with the device below, the area percentage of a peak area having peak top between the retention time 26.8 minutes to 27.1 minute relative to the total peak area (ref: the Figure).

In the GPC measurement, about 0.04 g of the sample was taken out, and the sample was subjected to methylurethane formation with methanol. Thereafter, excessive methanol was removed, and 10 mL of tetrahydrofuran was added to dissolve. The produced solution was subjected to GPC measurement with the following conditions.
(1) Analysis device: Alliance (Waters)
(2) Pump: Alliance 2695 (Waters)
(3) Detector: type 2414 refractive index detector (Waters)
(4) Eluent: Tetrahydrofuran
(5) Separation column: Plgel GUARD+Plgel 5 μm Mixed-C×3 (50×7.5 mm, 300×7.5 mm)
    Manufacturer; Polymer Laboratories
    Product number; PL1110-6500
(6) Measurement temperature: 40° C.
(7) Flow rate: 1 mL/min
(8) Sample injection amount: 100 μL
(9) Analysis device: EMPOWER data processing device (Waters)
System Correction
(1) Standard substance name: Polystyrene
(2) Calibration curve making method: using TSK standard Polystyrene having a different molecular weight manufactured by TOSOH, a graph for retention time versus molecular weight was made.
(3) Injection amount, injection concentration: 100 μL, 1 mg/mL A gel permeation chromatogram of the isocyanurate composition of Example 3 is shown in the Figure.

<Viscosity>

The viscosity was measured using a cone/plate viscometer (model: CV-1S, cone: 100P cone (angle: 2.0°, diameter: 14.5 mm), manufactured by Toa Industries, Ltd.), in conformity with corn and plate method of HS K5600-2-3 (2014) at a specific temperature (60° C., 80° C., 100° C.). The number of revolution of the cone and the plate at the time of measurement was changed in accordance with the increase in the viscosity to 750 rpm, 375 rpm, 1.88 rpm, 94 rpm, and 75 rpm accordingly.

<Production of Isocyanurate Composition>

Example 1

A reactor equipped with a thermometer, a stirrer, a nitrogen inlet tube, and a condenser tube was charged with 100 parts by mass of 1,3-xylylenediisocyanate (manufactured by Mitsui Chemicals, Inc., m-XDI), 0.025 phr of 2,6-di (tert-butyl)-4-methylphenol (also called: dibutylhydroxytoluene, BHT, hindered phenol antioxidant (stabilizer)), and 0.05 phr of tetraphenyl·dipropylene·glycol diphosphite (JPP-100 (trade name, manufactured by Johoku Chemical Co. Ltd.), organic phosphites, promoter) in a nitrogen atmosphere, and thereafter, to the liquid charged, as an isocyanurate-forming catalyst, 0.016 phr (active component (catalyst) 100% based: 0.006phr) of a 37mass % methanol solution of hydroxide of tetrabutylammonium (TBAOH) was blended, thereby causing reaction at a reaction start temperature of 60° C. Thereafter, during reaction, 0.0024 phr (active component (catalyst) 100% based: 0.009 phr) of 37 mass % methanol solution of hydroxide of tetrabutylammonium (TBAOH) was added, and the reaction was terminated at 120 minutes from the start of the reaction, thereby producing a reaction mixture liquid. The maximum temperature reached during the reaction was 68° C. The liquid charged had an isocyanate group concentration of 44.7 mass %, and the reaction mixture liquid had an isocyanate group concentration of 40.8 mass %.

The obtained reaction mixture liquid was passed through a thin film distillation device (temperature 150° C., degree of vacuum 50 Pa), and unreacted. 1,3-xylylenediisocyanate was removed, thereby producing an isocyanurate composition consisting of an isocyanurate derivative of 1,3-xylylenediisocyanate. The isocyanurate composition distillation yield was 16.1 mass %.

The isocyanate group conversion rate (isocyanurate conversion rate) in this reaction was 8.6 mass %.

The isocyanurate composition had a viscosity at 100° C. of (solid content 100 wt %) 700 mPa·s, a viscosity at 80° C. of 3100 mPa·s, and a viscosity at 60° C. of 13200 mPa·s.

The isocyanurate composition had an isocyanate group concentration (solid content 100 wt %) of 21.2 mass %, and the mononuclear content of 85 mass %.

Examples 2 to 8 and Comparative Examples 1 to 3

An isocyanurate composition consisting of an isocyanurate derivative was produced in the same manner as in Example 1, except that the formulation and production conditions were changed according to Tables 1 to 3.

The formulation, production conditions, and characteristics of the isocyanurate composition produced in Examples 1 to 8 and Comparative Examples 1 to 3 are shown in Tables 1 to 3.

The viscosity at 60° C. of Examples 4 to 8 and Comparative Example 3, and the viscosity at 80"C of Example 8 are not shown because these could not be measured.

The distillation yield, the isocyanate group concentration, the viscosity (100° C., 80° C., 60° C.) and the mononuclear content of the isocyanurate composition of Comparative Example 2 are not shown because gelation occurred in the isocyanurate composition of Comparative Example 2 after allowing it to stand for a night, and therefore could not be measured.

TABLE 1

| | | | | Example No. | | | |
|---|---|---|---|---|---|---|---|
| | | | | Example 1 | Example 2 | Example 3 | Example 4 |
| Formulation | Isocyanate | | Type | m-XDI | m-XDI | m-XDI | m-XDI |
| | | | Parts by mass | 100 | 100 | 100 | 100 |
| | | | Type | — | — | — | — |
| | | | Parts by mass | — | — | — | — |

TABLE 1-continued

|  |  |  | Example 1 | Example 2 | Example 3 | Example 4 |
|---|---|---|---|---|---|---|
|  | Isocyanurate-forming catalyst (active component 100%) | Type | TBAOH | TBAOH | TBAOH | TBAOH |
|  |  | phr (initial period) | 0.006 | 0.006 | 0.003 | 0.003 |
|  |  | phr (additional) | 0.009 | 0.009 | 0.015 | 0.018 |
|  |  | phr (total) | 0.015 | 0.015 | 0.018 | 0.021 |
|  | Promoter | Type | JPP-100 | JPP-100 | JPP-100 | JPP-100 |
|  |  | phr | 0.05 | 0.05 | 0.05 | 0.05 |
|  | Antioxidant | Type | BHT | BHT | BHT | BHT |
|  |  | phr | 0.025 | 0.025 | 0.024 | 0.025 |
| Production conditions | Reaction start temperature (° C.) |  | 60 | 60 | 70 | 60 |
|  | Highest temperature reached (° C.) |  | 68 | 77 | 77 | 72 |
|  | Reaction time (min) |  | 120 | 140 | 300 | 480 |
|  | Distillation yield (mass %) |  | 16.1 | 22.2 | 31.5 | 57.4 |
| Characteristics | Isocyanate group concentration of liquid charged (mass %) |  | 44.7 | 44.7 | 44.7 | 44.7 |
|  | Isocyanate group concentration of reaction mixture liquid (mass %) |  | 40.8 | 39.3 | 35.9 | 30.4 |
|  | Isocyanate group concentration of isocyanurate composition (mass %) |  | 21.2 | 21.2 | 20.5 | 20.5 |
|  | Isocyanurate conversion rate (mass %) |  | 8.6 | 11.9 | 19.6 | 31.9 |
|  | Viscosity (mPa · s) | 100° C. | 710 | 980 | 2300 | 5800 |
|  |  | 80° C. | 3100 | 4800 | 11500 | 45700 |
|  |  | 60° C. | 13200 | 20500 | 48400 | — |
|  | Mononuclear content (mass %) |  | 85 | 80 | 67 | 55 |

TABLE 2

|  |  |  | Example 5 | Example 6 | Example 7 | Example 8 |
|---|---|---|---|---|---|---|
| Formulation | Isocyanate | Type | m-XDI | m-XDI | m-XDI | m-XDI |
|  |  | Parts by mass | 100 | 100 | 100 | 100 |
|  |  | Type | — | — | — | — |
|  |  | Parts by mass | — | — | — | — |
|  | Isocyanurate-forming catalyst (active component 100%) | Type | TBAOH | TBAOH | TBAOH | TBAOH |
|  |  | phr (initial period) | 0.003 | 0.003 | 0.003 | 0.003 |
|  |  | phr (additional) | 0.017 | 0.015 | 0.015 | 0.012 |
|  |  | ph r(total) | 0.020 | 0.018 | 0.018 | 0.015 |
|  | Promoter | Type | JPP-100 | JPP-100 | JPP-100 | JPP-100 |
|  |  | phr | 0.05 | 0.05 | 0.05 | 0.05 |
|  | Antioxidant | Type | Irg1076 | Irg1076 | BHT | BHT |
|  |  | phr | 0.025 | 0.025 | 0.024 | 0.024 |
| Production conditions | Reaction start teraperature (° C.) |  | 64 | 60 | 60 | 60 |
|  | Highest temperature reached (° C.) |  | 77 | 77 | 79 | 79 |
|  | Reaction time (min) |  | 465 | 470 | 495 | 510 |
|  | Distillation yield (mass %) |  | 59.0 | 61.1 | 62.2 | 63.8 |
| Characteristics | Isocyanate group concentration of liquid charged (mass %) |  | 44.7 | 44.7 | 44.7 | 44.7 |
|  | Isocyanate group concentration of reaction mixture liquid (mass %) |  | 29.4 | 28.0 | 27.1 | 26.2 |
|  | Isocyanate group concentration of isocyanurate composition (mass %) |  | 19.5 | 17.4 | 16.5 | 15.8 |
|  | Isocyanurate conversion rate (mass %) |  | 34.1 | 37.3 | 39.4 | 41.4 |
|  | Viscosity (mPa · s) | 100° C. | 7300 | 9800 | 13000 | 19700 |
|  |  | 80° C. | 69100 | 87400 | 103200 | — |
|  |  | 60° C. | — | — | — | — |
|  | Mononuclear content (mass %) |  | 51 | 42 | 36 | 30 |

TABLE 3

|  |  |  | Comparative Example 1 | Comparative Example 2 | Comparative Example 3 |
|---|---|---|---|---|---|
| Formulation | Isocyanate | Type | m-XDI | m-XDI | m-XDI |
|  |  | Parts by mass | 100 | 100 | 95 |
|  |  | Type | — | — | p-XDI |
|  |  | Parts by mass | — | — | 5 |
|  | Isocyanurate-forming catalyst | Type | TBAOH | TBAOH | TBAOH |
|  |  | phr (initial period) | 0.003 | 0.003 | 0.003 |

TABLE 3-continued

|  |  |  | Comparative Example 1 | Comparative Example 2 | Comparative Example 3 |
|---|---|---|---|---|---|
|  | (active component 100%) | phr (additional) | 0.009 | 0.012 | 0.017 |
|  |  | phr (total) | 0.012 | 0.015 | 0.020 |
|  | Promoter | Type | JPP-100 | JPP-100 | JPP-100 |
|  |  | phr | 0.05 | 0.05 | 0.05 |
|  | Antioxidant | Type | BHT | BHT | Irg1076 |
|  |  | phr | 0.025 | 0.024 | 0.025 |
| Production conditions | Reaction start temperature (° C.) |  | 60 | 60 | 64 |
|  | Highest temperature reached (° C.) |  | 65 | 78 | 78 |
|  | Reaction time (min) |  | 100 | 530 | 450 |
|  | Distillation yield (mass %) |  | 9.3 | — | 58.7 |
| Characteristics | Isocyanate group concentration of liquid charged (mass %) |  | 44.7 | 44.7 | 44.7 |
|  | Isocyanate group concentration of reaction mixture liquid (mass %) |  | 42.4 | 25.2 | 29.5 |
|  | Isocyanate group concentration of isocyanurate composition (mass %) |  | 21.3 | — | 19.6 |
|  | Isocyanurate conversion rate (mass %) |  | 5.0 | 43.5 | 33.9 |
|  | Viscosity (mPa · s) | 100° C. | 510 | — | 7600 |
|  |  | 80° C. | 2000 | — | 68200 |
|  |  | 60° C. | 8700 | — | — |
|  | Mononuclear content (mass %) |  | 88 | — | 52 |

Details of abbreviation in Tables 1 to 3 are shown below.
m-XDI: 1,3-xylylenediisocyanate (manufactured by Mitsui Chemicals, Inc.)
p-XDI: 1,4-xylylenediisocyanate (manufactured by Mitsui Chemicals, Inc.)
TBAOH: 37 mass % methanol solution of hydroxide of tetrabutylammoniwn
JPP-100: tetraphenyl dipropylene diphosphite (aromatic organic phosphite, manufactured by Johoku Chemical Co. Ltd., trade name)
BHT: 2,6-di (tert-butyl)-4-methylphenol (hindered phenol antioxidant (stabilizer))
Irg1076: IRGANOX 1076 (hindered phenol antioxidant (stabilizer), manufactured by Ciba Japan K.K., trade name)

Comparative Example 4

Commercially available trimethylolpropane modified xylylenediisocyanate (trade name: D-110N, NCO group content: 11.5 wt %, solid content 75 wt %, solvent: ethyl acetate, viscosity (25° C.): 500 mPa·s, manufactured by Mitsui Chemicals, Inc.) was used as is.

Comparative Example 5

Commercially available isocyanurate derivative of 1,6-hexamethylene diisocyanate (trade name: D-170N, NCO group content: 20.7 wt. %, solid content 100 wt %, viscosity (25° C.): 200 m·Pas, manufactured by Mitsui Chemicals, Inc.) was used as is.

Comparative Example 6

Commercially available isocyanurate derivative of bis (isocyanatomethyl) cyclohexane (trade name: D-127N. NCO group content: 13.5 wt %, solid content 75 wt %, solvent: ethyl acetate, viscosity (25° C.): 40 mPa·s, manufactured by Mitsui Chemkals,was used as is.

Table 4 shows characteristics of the isocyanurate composition of Examples 1 to 8 and Comparative Examples 1 to 6.
<Evaluation>
(Preparation of Coating Solution)
The isocyanurate composition produced in Examples and Comparative Examples was blended with acrylic polyol (manufactured by Mitsui Chemicals, Inc., trade name: OLESTER Q666, hereinafter abbreviated as Q666) so that the equivalent ratio (NCO/OH) of the hydroxyl group in the acrylic polyol relative to the isocyanate group in the isocyanurate composition was 1.0, and the mixture was diluted with a thinner (1:1:1 weight ratio mixture of ethyl acetate/propylene glycol monomethyletheracetate/butyl acetate) so that the solid content was 50 mass %. Thereafter, the mixture was stirred at 23° C. for 5 minutes. Furthermore, ultrasonic treatment was conducted for 10 minutes for defoaming, thereby producing a coating solution.

(Production of Urethane Film)
The coating solution produced by the above-described method was applied on a polymethyl methacrylate (PMMA) plate no that the dried film had a thickness of 40 μm, and on a glass plate so that the dried film had a thickness of 100 μm. The film were dried at 23° C. for 2 hours, and thereafter subjected to heat treatment at 80° C. for 30 minutes. Thereafter, the films were aged at 23° C. and under a relative humidity of 55% for 7 days, thereby producing urethane films on the PMMA plate and on the glass plate.

The produced films were used for physical property evaluation below.
<Physical Property Evaluation>
Using the coating solution and the urethane film of Examples and Comparative Examples, physical properties shown below are evaluated.
(Set to Touch Drying Time)
The coating solution was applied using an applicator so that the thickness (thickness before drying) was 100 μm on the glass plate. After the application, the time until there is no tack when touched with a finger was measured at 23° C. and under a relative humidity of 30%.
(Through-dry Time)
The coating solution was applied using an applicator so that the thickness (thickness before drying) was 100 μm on the glass plate. After the application, the time was measured until there is no fingerprint mark when a finger is pressed strongly at 23° C. and a relative humidity of 30%.
(Evaluation of Compatibility of Film Form)
The haze of the urethane film applied on the glass plate was evaluated with a haze meter (manufactured by Nippon Denshoku Industries Co., Ltd., NDH2000).

(Evaluation on Weatherability)

With a super accelerated weathering test instrument (Dewpanel Light Control Weather Meter, manufactured by Suga. Test Instruments Co., Ltd.), the urethane film applied on the PMMA plate was treated with cycles of daytime (60° C.×relative humidity 10%×4 hours×light irradiation), and night time (50° C.×relative humidity 95%×4 hours×no ligtht irradiation) for 600 hours. Gross was evaluated by a gross meter (manufactured by Nippon Denshoku Industries Co., Ltd., VG2000), gloss retention (after 600 hours) setting the initial gross as 100 was calculated.

Table 4 shows physical property evaluation of Examples and Comparative Examples.

The characteristics and evaluation of Comparative Example 2 are not shown because measurement was not possible because gelation occurred in the isocyanurate composition of Comparative Example 2.

Characteristics of D-110N, D-170N, and D-127N used in Comparative Examples 4 to 6 are not shown because measurement was not conducted.

While the illustrative embodiments of the present invention are provided in the above description, such is for illustrative purpose only and it is not to be construed as limiting in any manner. Modification and variation of the present invention that will be obvious to those skilled in the art is to be covered by the following claims.

INDUSTRIAL APPLICABILITY

The isocyanurate composition of the present invention is useful as a material of polyurethane resin, and the polyurethane resin produced from the isocyanurate composition of the present invention can be used in a wide range in various industrial fields.

The invention claimed is:

1. An isocyanurate composition consisting essentially of an isocyanurate derivative of 1,3-xylylenediisocyanate, and having a viscosity at 100° C. of 600 mPa·s or more and 20000 mPa·s or less.

TABLE 4

|  |  | Example No. ||||| 
| --- | --- | --- | --- | --- | --- | --- |
|  |  | Example 1 | Example 2 | Example 3 | Example 4 | Example 5 |
| Characteristics | Viscosity (mPa · s/100° C.) | 710 | 980 | 2300 | 5800 | 7300 |
|  | Isocyanurate conversion rate (mass %) | 8.6 | 11.9 | 19.6 | 31.9 | 34.1 |
|  | Mononuclear isocyanurate content (mass %) | 85 | 80 | 67 | 55 | 51 |
| Evaluation | Haze | 0.3 | 0.3 | 0.3 | 1.1 | 1.3 |
|  | Set to touch drying time (sec) | 145 | 135 | 115 | 100 | 95 |
|  | Through-dry time (min) | 120 | 120 | 105 | 95 | 90 |
|  | Gloss retention (%) | 83 | 85 | 91 | 90 | 90 |

|  |  | Example No./Comparative Example No. |||||
| --- | --- | --- | --- | --- | --- | --- |
|  |  | Example 6 | Example 7 | Example 8 | Comparative Example 1 | Comparative Example 2 |
| Characteristics | Viscosity (mPa · s/100° C.) | 9800 | 13000 | 19700 | 510 | — |
|  | Isocyanurate conversion rate (mass %) | 37.3 | 39.4 | 41.4 | 5.0 | 43.5 |
|  | Mononuclear isocyanurate content (mass %) | 42 | 36 | 30 | 88 | — |
| Evaluation | Haze | 2.1 | 5.0 | 5.4 | 0.3 | — |
|  | Set to touch drying time (sec) | 90 | 90 | 90 | 185 | — |
|  | Through-dry time (min) | 85 | 85 | 85 | 150 | — |
|  | Gloss retention (%) | 88 | 83 | 81 | 81 | — |

|  |  | Comparative Example No. ||||
| --- | --- | --- | --- | --- | --- |
|  |  | Comparative Example 3 | Comparative Example 4 | Comparative Example 5 | Comparative Example 6 |
| Characteristics | Viscosity (mPa · s/100° C.) | 7600 | — | — | — |
|  | Isocyanurate conversion rate (mass %) | 33.9 | — | — | — |
|  | Mononuclear content (mass %) | 52 | — | — | — |
| Evaluation | Haze | 19.8 | 0.3 | 0.3 | 0.3 |
|  | Set to touch drying time (sec) | 100 | 155 | 150 | 170 |
|  | Through-dry time (min) | 95 | 125 | 140 | 140 |
|  | Gloss retention (%) | 75 | 51 | 99 | 99 |

Details of abbreviation in Table 4 are shown below.

D-110N: trimethylolpropane modified xylylenediisocyanate (NCO group content: 11.5 wt %, solid content 75 wt %, sol vent: ethyl acetate, viscosity (25° C.): 500 mPa·s, manufactured by Mitsui Chemicals, Inc.)

D-170N: isocyanurate derivative of 1,6-hexamethylene diisocyanate (NCO group content: 20.7 wt %, solid content 100 wt %, viscosity (25° C.): 200 mPa·s, manufactured by Mitsui Chemicals, Inc.)

D-127N: isocyanurate derivative of bis(isocyanatomethyl)cyclohexane (NCO group content: 13.5 wt %, solid content 75 wt %, solvent: ethyl acetate, viscosity (25° C.): 40 mPa·s, manufactured by Mitsui Chemicals, Inc.)

2. The isocyanurate composition according to claim 1, wherein the isocyanurate composition has a viscosity at 100° C. of 1500 mPa·s or more and 12000 mPa·s or less.

3. The isocyanurate composition according to claim 1, wherein the mononuclear isocyanurate content relative to a total amount of the isocyanurate composition is 30 mass % or more and 85 mass % or less.

4. The isocyanurate composition according to claim 3, wherein the mononuclear isocyanurate content relative to a total amount of the isocyanurate composition is 40 mass % or more and 70 mass % or less.

* * * * *

UNITED STATES PATENT AND TRADEMARK OFFICE
CERTIFICATE OF CORRECTION

PATENT NO. : 9,725,422 B2
APPLICATION NO. : 15/123199
DATED : August 8, 2017
INVENTOR(S) : Kazuyuki Fukuda et al.

It is certified that error appears in the above-identified patent and that said Letters Patent is hereby corrected as shown below:

In the Specification

In Column 1, Line 18, delete "To he more specific" and insert --To be more specific--
In Column 1, Line 57, delete "12000 mPas" and insert --12000 mPa • s--
In Column 2, Lines 61-62, delete "trimethythydroxyethylammonium" and insert --trimethylhydroxyethylammonium--
In Column 3, Line 2, delete "and acetylacetonate;" and insert --and lithium acethylacetonate;--
In Column 3, Line 64, delete "0.1 pans by mass (phr) or less," and insert --0.1 parts by mass (phr) or less,--
In Column 5, Line 55, delete ""unmodified") be produced" and insert --"unmodified") can be produced--
In Column 6, Line 17, delete "160 mass %" and insert --16.0 mass %--
In Column 6, Line 36, delete "isocyarmrate" and insert --isocyanurate--
In Column 6, Line 52, delete "isocyarmrate" and insert --isocyanurate--
In Column 7, Line 18, delete "lower limn or more," and insert --lower limit or more,--
In Column 7, Line 32, delete "composition's preferably" and insert --composition is preferably--
In Column 7, Line 43, delete "area thereinafter trimolecular" and insert --area (thereinafter trimolecular--
In Column 8, Line 4, delete "properties described later)" and insert --properties (described later)--
In Column 8, Line 34, delete "dimethyl benzene" and insert --dimethylbenzene--
In Column 8, Lines 40-41, delete "N,N-dimethyl ethane" and insert --N,N-dimethylethane--
In Column 9, Line 63, delete "and 2000" and insert --and 20000--
In Column 10, Lines 16-17, delete "other polyisocyanate," and insert --other polyisocyanate.--
In Column 10, Line 37, delete "diethylene triethylene glycol," and insert --diethylene glycol, triethylene glycol,--
In Column 10, Line 67, delete "hydrogen group-contain/g" and insert --hydrogen group-containing--

Signed and Sealed this
Seventh Day of August, 2018

Andrei Iancu
*Director of the United States Patent and Trademark Office*

CERTIFICATE OF CORRECTION (continued)
U.S. Pat. No. 9,725,422 B2

| | | |
|---|---|---|
| In Column 11, | Line 7, | delete "am group, etc.)" and insert --amino group, etc.)-- |
| In Column 11, | Line 9, | delete "For the polymerizatio method," and insert --For the polymerization method,-- |
| In Column 11, | Line 62, | delete "(e.,c;., hydroxyl group," and insert --(e.g., hydroxyl group,-- |
| In Column 12, | Line 60, | delete "drying properties," and insert --drying properties.-- |
| In Column 13, | Line 48, | delete "component main component)," and insert --component (main component),-- |
| In Column 13, | Line 49, | delete "polyol component s used." and insert --polyol component is used.-- |
| In Column 15, | Line 45, | delete "HS K5600-2-3 (2014)" and insert --JIS K5600-2-3 (2014)-- |
| In Column 15, | Line 49, | delete "1.88 rpm," and insert --188 rpm-- |
| In Column 16, | Line 49, | delete "at 80"C of Example 8" and insert --at 80°C of Example 8-- |
| In Column 19, | Line 31, | delete "tetrabutylammoniwn" and insert --tetrabutylammonium-- |
| In Column 19, | Line 53, | delete "m • Pas," and insert --mPa • s,-- |
| In Column 21, | Line 58, | delete "sol vent:" and insert --solvent:-- |